(12) United States Patent
Jaggi et al.

(10) Patent No.: US 6,403,816 B1
(45) Date of Patent: Jun. 11, 2002

(54) BETULINIC ACID DERIVATIVES HAVING ANTIANGIOGENIC ACTIVITY, PROCESSES FOR PRODUCING SUCH DERIVATIVES AND THEIR USE FOR TREATING TUMOR ASSOCIATED ANGIOGENESIS

(75) Inventors: Manu Jaggi, Haryana; Sunder Ramadoss, New Delhi; Praveen Rajendran, Ghaziabad; Mohammad Jamshed Ahmad Siddiqui, Delhi, all of (IN)

(73) Assignee: Dabur Research Foundation, Ghaziabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 09/399,617

(22) Filed: Sep. 20, 1999

Related U.S. Application Data

(63) Continuation-in-part of application No. 09/040,856, filed on Mar. 18, 1998, now Pat. No. 6,048,847.

(30) Foreign Application Priority Data

Sep. 30, 1997 (IN) ................................. 2801/97

(51) Int. Cl.$^7$ ................................................ C07J 53/00
(52) U.S. Cl. ...................................................... 552/510
(58) Field of Search .......................................... 552/510

(56) References Cited

U.S. PATENT DOCUMENTS 5,468,888 A * 11/1995 Bouboutou et al. ........... 554/58
6,048,847 A *  4/2000 Ramadoss et al. .......... 514/169

OTHER PUBLICATIONS

Klinot et al., "3,4–seco derivatives of betulinic acid," Coll. Czech. Chem. Comm., vol. 37, pp. 60–609, 1972.*

* cited by examiner

Primary Examiner—Barbara P. Badio
(74) Attorney, Agent, or Firm—Ladas & Parry

(57) ABSTRACT

The invention relates to novel betulinic acid derivatives having antiangiogenic activity, processes for producing such derivatives and their use for treating tumor associated angiogenesis.

1 Claim, No Drawings

BETULINIC ACID DERIVATIVES HAVING ANTIANGIOGENIC ACTIVITY, PROCESSES FOR PRODUCING SUCH DERIVATIVES AND THEIR USE FOR TREATING TUMOR ASSOCIATED ANGIOGENESIS

This application is a continuation-in-part of U.S. application Ser. No. 09/040,856 filed Mar. 18, 1998 now U.S. Pat. No. 6,048,847.

FIELD OF THE INVENTION

This invention relates to novel betulinic acid derivatives and a composition containing betulinic acid derivatives, processes for preparation of such betulinic acid derivatives and method of treatment of tumor and such proliferative disease using these derivatives. This invention also relates to the use of the novel betulinic acid derivatives for inhibiting and/or preventing tumor associated angiogenesis, more specifically angiogenesis associated with prostate, lung, ovary and colon cancers.

BACKGROUND OF THE INVENTION

Betulinic acid is a pentacyclic triterpene. It can derived from several natural (botanical) sources. It can also be chemically derived from betulin, a substance found in abundance in the outer bark of white birch trees (Betula alba). Betulinic acid has been found to selectively kill human melanoma cells (Nature Medicine, Vol.1(10),1995, WO 96/29068). The cytotoxic potential of betulinic acid was tested using three human melanoma cell lines, Mel-1, Mel-2, and Mel-4. The growth of all the cell lines was inhibited significantly by treatment with betulinic acid. The effectiveness of betulinic acid against melanoma cancer cells was also tested using athymic mice. It seems to work by inducing apoptosis in cancer cells.

The anti-cancer activity of betulinic acid and some of its derivatives has also been demonstrated using mouse sarcoma 180 cells implanted s.c. in nude mouse (JP 87,301, 580), inhibition of growth of p388 lymphocytic leukemia cells in vitro (Choi.Y-H et al., Planta Medica Vol.XLVII, 511–513,1988) and inhibiting growth of cancer cells, particularly by inhibiting ornithine decarboxylase (Yasukawa, K et al, Oncology 48:72–76,1991; WO 95/04526).

Recently, the applicants reported anti-leukemia and anti-lymphoma activity and anti-prostate, anti-lung and anti-ovarian cancer activity of betulinic acid and its derivatives with $ED_{50}$ values less than 4.0 μg/ml. (U.S. application Ser. No. 09/040,856 filed on Mar. 18, 1998 and U.S. application Ser. No. 09/251,309 filed on Feb. 17, 1999). Further, anti-angiogenic activity of betulinic acid and its derivatives was recently reported by the applicants in U.S. application Ser No. 09/166,809 filed on Oct. 06, 1998 wherein betulinic acid and its derivatives were shown to inhibit the formation of tube-like-structures (TLS) of endothelial cells when grown on Matrigel coated surface. The endothelial cell anti-proliferative activity along with anti-TLS activity was shown to suggest the anti-angiogenic activity of betulinic acid derivatives.

Anderson et al (WO 95/04526) disclose that for certain cancers to spread throughout a patients' body, a process termed metastasis, cell-cell adhesion must take place. Specifically, cancer cells must migrate from their site of origin and gain access to blood vessel to facilitate colonization at distant sites. Certain cancer cells are known to adhere to E-Selectin via E-Selectin ligands on their cell surface and this event is one component of the metastasis process. Betulinic acid and its derivatives interfere with Selectin binding. Betulinic acid inhibited P-Selectin binding to 2,3, sLex, a chemical known: to bind to P-Selectin, with an $IC_{50}$ of 125 uM. Also it inhibited P-Selectin binding HL-60 cells in a dose-dependent way with an $IC_{50}$ of 0.75 mM. Betulinic acid and derivatives also significantly interfere with the binding to colon cancer cells, LS174T to E-Selectin.

Dasgupta et al (WO 96/29068) disclosed a method and composition for inhibiting tumor growth using the active compound betulinic acid. The invention provides a method and composition for inhibiting tumor growth and, particularly, for inhibiting growth of melanoma using a natural product derived compound. The invention also provides a treatment method using betulinic acid to prevent growth or spread of cancer cells, wherein betulinic acid is applied in a topical preparation.

Pezzuto et al (U.S. Pat. No. 5,869,535) disclose method and composition for probes inhibiting tumor growth using betulinic acid or a derivative thereof. Betulinic acid has been isolated from stem bark of Ziziphzus mauritiana, by mediating a selective cytotoxic profile against human melanoma in a subject panel of human cancer cell lines, conducting a bioassay directed fractionation based on the profile of bio-activity using cultured human melanoma cells (MEL-2) as the monitor, and betulinic acid has been obtained therefrom as the active compound. The resulting betulinic acid can be used to inhibit tumor growth or can be converted to a derivative to prevent which prevents or inhibits tumor growth. The invention also provides a treatment method using betulinic acid to present the growth or spread of cancerous cells, wherein betulinic acid or derivatives thereof is applied in a topical preparation. Betulinic acid was found to inhibit in vitro growth of MEL-2 cells. However, none of the other cell lines tested [A431 (squamous cells), BC-1 (breast), COL-2 (colon), HT1080 (sarcoma), KB (human oral epidermoid carcinoma), LNCaP (prostate), LU-1 (lung), U373 (glioma) and ZR-75-1 (breast)] were affected by betulinic acid (ie., $ED_{50}$ values of greater than 20 μg/ml).

Lee et al (WO 96/39033) disclose betulinic acid and dihydrobetulinic acid acyl derivative to have potent anti-HIV activity. The $C_3$-hydroxy, $C_{17}$-carboxylic acid and $C_{20}$-exomethylene groups have been modified. Anti-HIV assays indicate potent anti-HIV activity of betulinic acid and dihydrobetulinic acid derivatives in acutely infected H9 lymphocytes with $EC_{50}$ values of less than $1.7 \times 10^{-5}$ μM respectively.

OBJECTS OF THE INVENTION

The invention provides a method of treating angiogenesis by administering a pharmaceutically effective dosage of betulinic acid derivatives. This invention also provides for novel betulinic acid derivatives and compositions containing them with pharmaceutically acceptable additives, diluents, carriers and excipients with or without betulinic acid.

Another object of the invention relates to providing novel betulinic acid derivatives, which are used for inhibiting angiogenesis.

Another object of the invention is to provide a compound and compositions for treating, inhibiting and/or preventing angiogenesis using a natural product-derived compound and its derivatives.

Another object of the invention is to provide a treatment method using betulinic acid derivatives to inhibit angiogenesis, wherein the derivatives are administered systemically.

Yet another object of the invention is to overcome the problem of high toxicity associated with standard antiangiogenic chemotherapeutic agents by using a natural product-derived compound, e.g., betulinic acid or its derivatives.

Still another object of the invention is to overcome the problem of insufficient availability associated with synthetic antiangiogenic anticancer agents by using readily available semisynthetic derivatives of betulinic acid.

Another object of the invention is to overcome the problem of high costs of synthetic antiangiogenic agents by utilizing the readily available natural product derived compound. e.g. betulinic acid and its derivatives which is expected to be less expensive than other chemotherapeutic drugs.

These and other objects of the present invention will become apparent from the description of the invention disclosed below, which descriptions are intended to limit neither the spirit or scope of the invention but are only offered as illustrations of the preferred embodiments of the invention.

SUMMARY OF THE INVENTION

The above objects and others have been achieved by providing novel betulinic acid derivatives of formulae 1 and 2 which are described in the present description.

DETAILED DESCRIPTION OF THE INVENTION

The present invention provides a pharmaceutical composition useful for preventing/inhibiting angiogenesis. Betulinic acid derivatives inhibit endothelial cell proliferation and exhibiting high endothelial cell specificity thereby specifically targeting endothelial cells. The derivatives also inhibit the formation of tube-like-structures (TLS) of endothelial cells when grown on Matrigel coated surface. The endothelial cell anti-proliferative activity along with anti-TLS activity very strongly suggests the anti-angiogenic activity of betulinic acid derivatives.

The method comprises administering a therapeutically effective dose betulinic acid derivatives other alone or in a pharmaceutical composition containing the compounds so as to kill, inhibit or prevent the multiplication of tumor associated endothelial cells. In a preferred embodiment, pharmaceutically acceptable carriers, diluents, excipients and/or solvents are used with betulinic acid/or its derivatives. The method of treatment of the present invention may be particularly useful in inhibiting angiogenesis.

The novel derivatives of betulinic acid have a basic skeleton of betulinic acid as shown herebelow in Figure 1.

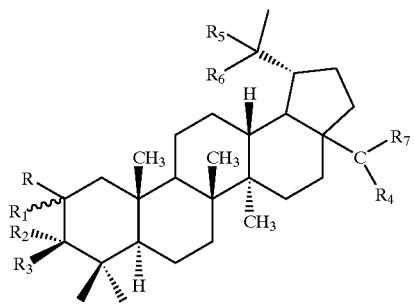

FIG.-1 wherein R, $R_1$ $R_2$, $R_3$, $R_4$, $R_5$, $R_6$ and $R_7$ independently or in combination represent the following groups:

R is H;

$R_1$ is H, Br, Cl, F or I;

$R_2$ is H and $R_3$ is OH, $OCO(CH_2)_nCH_3$ (where n=0 to 14), $OCOC(CH_3)_3$, $OCO(CH_2)_nX$ (where n=1 to 7, X=H, Cl, Br, F), $OCOCH_2C_6H_nX$ [n=2 to 4, X=H, Cl, Br, F, I, CN, $NO_2$, $NH_2$, $CF_3$, $CHCl_2$, OH, $OCH_3$, $OC_2H_5$, $CHCl_2$ or $C_nH_{2n+1}$(n=1 to 7)], $OSO_2(CH_2)_nX$ (where n=1 to 7, X=H or Cl), $OSO_2ONH_2$, $OCOC_6H_nX$ [n=0 to 4, X=H, Cl, Br, F, I, CN, $NO_2$, $NH_2$, $CF_3$, OH, $OCH_3$, $OC_2H_5$, $CHCl_2$ or $C_nH_{2n+1}$(n=1 to 7)], $NH_2$, $NH(CH_2)_n$ OR [(n=2 to 4), R=H or $COCH_3$], NHR, $N(R)^2$ [where $R=CH_3$, $C_2H_5$, $C_3H_7$, $C_4H_9$], $NHC_6H_nX$, $NHCH_2C_6H_nX$ (where n=2 to 4), $NHCH_2C_{10}H_nX$ (n=2 to 7) [X=H,Cl, Br, F, I, $CHCl_2$, CN, $CF_3$, $CHCl_2$, OH, $OCH_3$, $OC_2H_5$ or $C_nH_{2n+1}$(n=1 to 7)], $RCH_2NOH$ (R=H,$CH_3$,$C_2H_5$,$C_3H_7$,$C_4H_9$), NHOR (R=H, $COCH_3$, $COC_6H_nX$, $OCH_2C_6H_nX$, $OC_6H_nX$) [n=2 to 4, X=Cl, Br, F, I, $CF_3$, $CHCl_2$, CN, $NO_2$, $CH_3$, $NH_2$, OH, $OCH_3$, $OC_2H_5$ or $C_nH_{2n+1}$(n=1 to 7)], $N=CHC_6H_nX$ (where n=2 to 4), $N=CHC_{10}H_nX$ (n=2 to 6)[X=H, Cl, Br, F, I, $CF_3$, CN, $NO_2$, NH2, OH, $OCH_3$, $OC_2H_5$ or $C_nH_{2n+1}$ (n=1 to 3)], $OCO(CH_2)_nNH_2$ (n=2 to 8), $NHCO(CH_2)_n$ X (X=H,Cl or Br, n=1 to 4), $NHCOC_6H_nX$, $NHCOC_{10}H_nX$ (n=2 to 6), $NHCOCH_2C_6H_nX$ (n=2 to 4), $NHCOCH_2C_{10}H_nX$ (n=2 to 6)[X=Cl, Br, F, I, $CF_3$, CN, $NO_2$, $NH_2$, OH, $OCH_3$, $OC_2H_5$, $CHCl_2$ or $C_nH_{2n+1}$ (n=1 to 7)], $NHCOC_6H_4COOH$, $NHCOC_6H_n$ (COOH)X [where n=2 or 3, X=H, Cl, Br, F, $NO_2$ or $NH_2$), $OCOC_6H_4COOH$, $OCOC_6H_n(COOH)X$ (where n=2 or 3, X=H, Cl, Br, F, $NO_2$ or $NH_2$), $OCOCHRR_1$, (R=H, $CH_3$ or Ph; $R_1$=OH, Cl, Br or $OCOCH_3$), $NHNHC_6H_nX$ (n=2 to 4), $NHNHCH(OH)C_6H_nX$ (n=2 to 4), $NHNHC_{10}H_nX$ (n=2 to 6), NHNHCH(OH)$C_{10}H_nX$ (n=2 to 6)[X=Cl, Br, F, I, OH, $OCH_3$, $OC_2H_5$, $NO_2$, $NH_2$, $CHCl_2$, $CF_3$ or $C_nH_{2n+1}$(n=1 to 7)], $OCOCH=C(R)^2$ (R is H, $CH_3$ or $C_2H_5$), O—CO—CH=CH—COOH, O—CO—C(Br)=CHCOOH, $OCOCH_2C(R)^2COOH$ (R=H or $CH_3$), $OCO(CH_2)_n$ COOH (n=0 to 3),

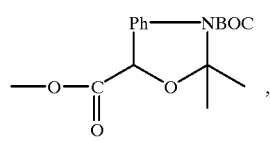, 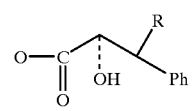

[R=$NH_2$, $NHC_6H_nX$ (n=2 to 4), $NHC_{10}H_nX$ (n=2 to 6), $NHCO(CH_2)_nX$ (n=1 to 16)[X=H, Cl, F, Br], $NHCOC_6H_nX$, $NHCOCH_2C_6H_nX$ (n=2 to 4), $NHCOC_{10}H_nX$ (n=2 to 6), $N=CHC_6H_nX$ (n=2 to 4), $N=CHC_{10}H_nX$ (n=2 to 6), $NHCH_2C_6H_nX$ (n=2 to 4), $NHCH_2C_{10}H_nX$ (n=2 to 6)[X=H, Cl, Br, F, I, CN, $NO_2$, $NH_2$, $CF_3$, $CHCl_2$, $OCH_3$, $OC_2H_5$ or $C_nH_{2n+1}$ (n=1 to 7), $NHSO_2(CH_2)_nX$ (n=1 to 7), $NHSO_2C_6H_nX$ (n=2 to 4)[X=H, Cl, Br, F, $CH_3$, $NO_2$ or $NH_2$], $R_2$ and $R_3$ together are O, $NNHC_6H_nX$, $NNHCOC_6H_nX$ (n=2 to 4), $NNHC_{10}H_nX$ (n=2 to 6), $NNHCOC_6H_nX$ (n=2 to 6), $NC_6H_nX$ (n=2 to 4), $NC_{10}H_nX$ (n=2 to 6), [X=H, Cl, Br, F, I, CN, NO, $NO_2$, $NH_2$, $CF_3$, $CHCl_2$, OH, $OCH_3$, $OC_2H_5$ or $C_nH_{2n+1}$ (n=1 to 7)], $NNHC_6H_nBrX$ [(n=2 or 3), X=F, Cl, $NO_2$, $NH_2$, $OCH_3$, $OC_2H_5$, $C_nH_{2n+1}$ (n=1 to 7)], $NOSO_3H$, N—OX, NHOX [X being H, $CH_3$, $C_2H_5$, $COCH_3$, $SO_2C_6H_4CH_3$, $COC_6H_nX$, $C_6H_nX$, $CH_2C_6H_nX$ [(n=2 to 4) X=H, Cl, Br, F, I, CN, $NO_2$, $NH_2$, OH, $OCH_3$, $OC_2H_5$, $C_nH_{2n+1}$ (n=1 to 7]. $CF_3$ or $CHCl_2$], NNHR [R is $CH_3$, $C_2H_5$, $C_2H_4OY$, Y=H, alkyl, phlenyl, benzyl or its substituted derivative with Cl, Br, F, I, $NO_2$, $NH_2$, $CF_3$, $CHCl_2$, OH, $OCH_3$, $OC_2H_5$ or $C_nH_{2n+1}$ (n=1 to 7)], $R_7$ is O and $R_4$ is H, OH, Cl, $N_3$, $NH_2$, OR (R=$CH_3$, $C_2H_5$, $C_3H_7$, $C_4H_9$), $O(CH_2)_nCOY$ (n=1 to 3)[Y=OH, $OCH_3$, $OC_2H_5$, Cl, CN, $N_3$, $NH_2$], $OCH_2CH_2OY$ [Y=H, $CH_3$, $C_2H_5$, $COCH_3$], $OCOCH=C(R)^2$ (R=H, $CH_3$ or $C_2H_5$), $OCO(CH_2)_nX$ (n=1 to 16), (X=H, Cl, F or Br), $OCOC_6H_nX$ (n=0 to 4), $OCOCH_2C_6H_nX$ (n=2 to 4)[X=H, Cl, Br, F, I, CN, $NO_2$, $CF_3$, $CHCl_2$, OH, $OCH_3$, $OC_2H_5$ or $C_nH_{2n+1}$ (n=1 to 7)], $NH(CH_2)_nCH_3$ (n=0 to 9), $NH(CH_2)_nCOOH$ (n=1 to 8), $OCH_2CHO$, $OCH_2CH=NOX$, $OCH_2CH_2NHOX$[X=H, $CH_3$, $SO_2C_6H_4CH_3$, $OCOCH_3$, $OCOC_6H_5$, phenyl or benzyl substituted derivatives], $OCH_2CH=NNHC_6H_nX$, $OCH_2CH_2NHNHC_6H_nX$ (n=2 to 4), $OCH_2CH=NNHC_{10}H_nX$ (n=2 to 6), $OCH_2CH_2CH_2NHNHC_{10}H_nX$ [X=H, Cl, Br, F, I, CN, $CF_3$, $CHCl_2$, $NO_2$, $NH_2$, OH, $OCH_3$, $OC_2H_5$ or $C_nH_{2n+1}$ (n=1 to 7)], $OCH_2CH_2N(R)^2$ (R=H, $CH_3$, $C_2H_5$, $C_3H_7$, $C_4H_9$, $C_6H_5$, $C_6H_5CH_2$ or its substituted derivative e.g.: Cl, Br, CN, F, I, $NO_2$, $NH_2$, $CF_3$, $CHCl_2$, OH, $OCH_3$, $OC_2H_5$ or $C_nH_{2+1}$ (n=1 to 7)], $R_4$ is H and $R_7$ is NOH, NHOR, N—OR [R is H, $CH_3$, $C_2H_5$, $SO_2C_6H_4CH_3$, $COCH_3$, $CH_2C_6H_nX$, $COC_6H_nX$ (n=2 to 4), X=Cl, Br, F, I, CN, $NO_2$, $NH_2$, OH, $OCH_3$, $OC_2H_5$, $CF_3$, $CHCl_2$ or $C_nH_{2n+1}$ (n=1 to 7)], $RCH_2NOH$ (R=H, $CH_3$ or $C_2H_5$), $NH_2$, $NHSO_2(CH_2)_nX$ (n=1 to 7), $NHSO_2C_6H_nX$ (n=2 to 5)[X=H, Cl, Br, $CH_3$, $NO_2$ or $NH_2$], $(NR)^2$ (R is H, $CH_3$, $C_2H_5$, $C_3H_7$, $C_4H_9$, Phenyl or Benzyl or its substituted derivative), $N=CHC_6H_nX$, $NHCH_2C_6H_nX$ (n=2 to 4), $N=CHC_{10}H_nX$, $NHCH_2C_{10}H_n$[X (n=2 to 6) X=H, Cl, Br, F, I, CN, $NO_2$, $NH_2$, $CF_3$, $CHCl_2$, OH, $OCH_3$, $OC_2H_5$ or $C_nH_{2n+1}$ (n=1 to 7)], $NNHC_6H_nX$, $NHNHC_6H_nX$, $NHNHCH(OH)C_6H_nX$, $NNHCOC_6H_nX$ (n=2 to 4), $NNHC_{10}H_nX$, $NNHCOC_{10}H_nX$, $NHNHC_{10}HnX$, $NHNHCH(OH)C_{10}HnX$ [where n=2 to 6, X=H, Cl, Br, F, I, CN, $NO_2$, $NH_2$, OH, $OCH_3$, $OC_2H_5$, $C_nH_{2n+1}$ (n=1 to 7)], NHCOR [R is $CH_3$, $CH_2Cl$, $CHCl_2$, $CCl_3$, $C_2H_5$, $C_2H_4Cl$, $C_3H_7$, $C_3H_6OH$, $C_3H_6Cl$, $C_6H_5$, $C_6H_nX$, $CH_2C_6H_nX$, $COCH_2C_6H_nX$ (n=2 to 4), $C_{10}H_nX$, $CH_2C_{10}H_nX$, $COCH_2C_{10}H_nX$ (n=2 to 6), X=Cl, Br, CN, F, I, $NO_2$, $NH_2$, $CF_3$, OH, $OCH_3$, $OC_2H_5$, $CHCl_2$ or $C_nH_{2n+1}$ (n=1 to 7)], $R_5$ is H or Br, $R_6$ is $CH_3$, $CH_2Br$, $CH_2OR$ [R is $CO(CH_2)_nX$, (n=1 to 7: X=H, Cl, Br or F), CHO, CHNOY, $CH_2NHOY$, [Y=H, $CH_3$, $C_2H_5$, $SO_2C_6H_5$, $SO_2C_6H_4CH_3$, $CH_2C_6H_nX$, $C_6H_nX$ (n=2 to 4), X=H, Cl, Br, F, I, CN, $NO_2$, $NH_2$, $CF_3$, $CHCl_2$, OH, $OCH_3$, $OC_2H_5$, $C_nH_{2n+1}$ (n=1 to 7)], $RCH_2NOH$ [where R is H, $CH_3$, $C_2H_5$, $C_3H_7$, $C_4H_9$], $CH_2NH_2$, $CH_2NHR$ or $CH_2N(R)^2$ [R is $CH_3$, $C_2H_5$, $C_3H_7$, $C_4H_9$, $C_6H_5$, $C_6H_nX$ or $CH_2C_6H_nX$, $COCH_2C_6H_nX$ (n=2 to 4), $CH_2C_{10}H_nX$, $COCH_2C_{10}H_nX$ (n=2 to 6)[X=H, Cl, Br, F, CN, I, $NO_2$, $NH_2$, OH, $OCH_3$, $OC_2H_5$, $CF_3$, $CHCl_2$ or $C_nH_{2n+1}$ (n=1 to 7)], COOH, COCl, CONHR (R is alkyl or aryl substituted group), CO—OCOR (R is alkyl or aryl substituted group), $COCH_2COR$ (R is OH, $OCH_3$, $OC_2H_5$, $NH_2$ or Cl), $COCH_2CH_2OR$ [R is H, $CO(CH_2)_nX$ (n=1 to 16), $COC_6H_nX$, $COCH_2C_6H_nX$, (n=2 to 4, X=H, Cl, Br, CN, F, I, $NO_2$, $NH_2$, $CF_3$, $CHCl_2$, OH, $OCH_3$, $OC_2H_5$ or $C_nH_{2n+1}$ (n=1 to 7)], $COO(CH_2)_nH$ (n=1 to 5), $COO(CH_2)_nCOY$ (n=1 to 5, Y=OH, $OCH_3$, $OC_2H_5$, Cl or Br); $CH=NC_6H_nX$ (n=2 to 4), $CH=NC_{10}H_nX$ (n=2 to 6), $CH=NNHC_6H_nX$, $CH=NNHCOC_6H_nX$ (n=2 to 4), $CH=NNHC_{10}H_nX$, $CH=NNHCOC_{10}H_NX$ (n=2 to 6), $CH_2NHNHC_6H_nX$ (n=2 to 4), $CH_2NHNHC_{10}H_nX$ (n=2 to 6), $CH_2NHNHCH(OH)C_6H_nX$ (n=2 to 4), $CH_2NHNHCH(OH)C_{10}H_nX$ (n=2 to 6) [where X=H, Cl, Br, F, I, CN, $CF_3$, $NO_2$, $NH_2$, $CHCl_2$, OH, $OCH_3$, $OC_2H_5$ or $C_nH_{2n+1}$ (n=1 to 7)], $R_5$ and $R_6$ together is O, OH, $O(CH_2)_nX$ (n=1 to 6, X=H, Cl or Br), $OCOC_6H_nX$, $OCOCH_2C_6H_nX$ [n=2 to 5, X=Cl, Br, F, I, CN, $NO_2$, $NH_2$, $CF_3$, OH, $OCH_3$, $OC_2H_5$ or $C_nH_{2n+1}$ (n=1 to 7)], $O(CH_2)_nCOOH$ (n=1 to 3), NOR, NHOR (R=H, $CH_3$, $C_2H_5$, $C_3H_7$, $COCH_3$, $COC_6H_5$, phenyl or benzyl substituted derivatives), $NH_2$, $(NR)^2$ (R=H, $CH_3$, $C_2H_5$, $C_3H_7$, $C_4H_9$, $C_6H_nX$, $CH_2C_6H_nX$; n=2 to 5, X=Cl, Br, F, I, $CF_3$, CN, $NO_2$, $NH_2$, OH, $OCH_3$, $OC_2H_5$, $C_nH_{2n+1}$ (n=1 to 7)], NHCO$(CH_2)_nX$ [n=1 to 16, X=Cl or Br], $NHCOC_6H_nX$, $NHCOCH_2C_6H_nX$ (n=2 to 4), $NHCOC_{10}H_nX$, $NHCOCH_2C_{10}OH_nX$ (n=2 to 6) (X=Cl, Br, F, I, CN, $CF_3$, $NO_2$, $NH_2$, OH, $OCH_3$, $OC_2H_5$, $C_nH_{2n+1}$ (n=1 to 7)], $N=CHC_6H_nX$ (n=2 to 4), $N=CHC_{10}H_nX$ (n=2 to 6), $NHCH_2C_6H_nX$ (n=2 to 5), $NHCH_2C_{10}H_nX$ (n=2 to 6), $NNHC_6H_nX$, $NC_6H_nX$, $NHC_6H_nX$ (n=2 to 4), $NC_{10}H_nX$, $NHC_{10}H_nX$, $NNHC_{10}H_nX$ (n=2 to 6), $NNHCOC_6H_nX$ (n=2 to 4), $NNHCOC_{10}H_nX$ (n=2 to 6), NR [R=$C_6H_nX$ (n=2 to 5), $C_{10}H_nX$ (n=2 to 7)[X=H, Cl, Br, Cl, F, I, CN, $NO_2$, $NH_2$, $CF_3$, $CHCl_2$, $OCH_3$, $OC_2H_5$, OH or $C_nH_{2n+1}$ (n=1 to 7)].

Preparation of Betulinic Acid Derivatives.

The following procedures are either used alone or in combination to produce the derivatives of the present invention.

EXAMPLE 1

Preparation of 3-o-acyl Derivatives

Method I: Substrate in organic base is treated with suitable anhydride (saturated or unsaturated) at room temperature for approximately 4–16 hours. Examples of anhydrides that can be used in this process are represented by general formula $(RCH_2CO_2)O$ wherein R=H, $CH_3$, $C_2H_5$, etc. The reaction was worked by evaporation of the reaction mixture, addition of water and extraction with an organic solvent. The organic layer was dried over anhydrous sodium sulfate, evaporated and residue crystallized to yield the corresponding pure 3-o acyl derivatives respectively. Examples of organic bases that can be used in this method are TEA, pyrdine and DMPA.

Method II: Substrate in halogenated organic solvent was treated with suitable acyl chloride as in Method I. The reaction was worked up as described in Method I to yield the corresponding 3-o-acyl derivatives in the pure form. Examples of acyl chlorides that can be used are R (CH$_2$)$_n$ COCI wherein R=H, Cl, BH, I or F and n=1 to 16 or RCH$_2$ (CH)$_n$, XCOCI wherein R=H, X=OH, OCOCH$_3$ and n=1. The halogenated solvent may be selected from CCl$_4$ CH$_2$Cl$_2$, C$_6$H$_5$CH$_3$ or the like.

EXAMPLE 2

Preparation of 3-oxo-derivatives.

The substrate was dissolved in an organic solvent and conventional oxidizing agent was added under normal reaction conditions. The reaction was worked up as described in Method I to yield the corresponding 3-oxo derivatives in the pure form.

Example of oxidizing agents that can be vised are CrO$_3$/Py; CrO$_3$/H$_2$SO$_4$; CrO$_3$/AcOH or the like. The normal reaction condition is stirring the substrate with oxidizing agent at from 0° C. to room temperature for a few hours. The organic solvent may be selected from acetone CH$_2$Cl$_2$, AcOH, mixtures thereof or the like.

EXAMPLE 3

Preparation of 2, 20,29-tribromo 3-oxo Derivative

A-3-oxo betulinic acid derivative prepared according to the process of Example 3 was dissolved in halogenated organic solvent. To this was added dropwise liquid bromine dissolved in the same solvent and the temperature was maintained between 0–10° C. The reaction mixture was brought to room temperature and stirred for a few hours. The reaction was worked up as described in Method I of Example 2. The organic layer was washed with 5–10% aqueous alkaline solution and evaporated. The crystallized product yielded pure 2, 20, 29-tribromo-3-oxo derivatives. Examples of halogenated solvents that can be used are CCl$_4$,CH$_2$Cl$_2$, CHCl$_3$ and the like; Examples of aqueous alkaline solution that can be used are bicarbonate or carbonate of an alkali metal in water, and the like.

3-Oxo-derivative of betulinic acid, dihydrobetulinic acid or their derivatives can be used in the processes of Examples 3, 4, 5, 8, 10 and 14.

EXAMPLE 4

Preparation of 3-oximino Derivative

A 3-oxo derivative is mixed in an alcoholic solvent such a methanol, ethanol, propanol and the like. To this was added alkyl hydroxylamine, phenyl hydroxylamine or benzyl hydroxylamine or its substituted derivatives and sodium acetate. The mixture was refluxed for a few hours. The reaction mixture was evaporated to dryness. The reaction was worked up as described in Method I of Example 2 and yielded crude-3-oximino derivative which crystallized to yield the corresponding pure 3-oximino derivative.

EXAMPLE 5

Preparation of Phenylhydrazone of 3-oxo Derivative

Phenylhydrazine or alkyl hydrazine their substituted analogs or a salt thereof, and sodium acetate were added to 3-oxo derivative dissolved in alcoholic solvent such as methanol, ethanol, propanol and the like, and was refluxed for about four hours. The reaction was worked up as described in Method I of Example 2 to yield the corresponding pure phenylhydrazone derivative in pure form.

EXAMPLE 6

Preparation of 17 and/or 20-carboxyalkyl Carboxylate

To the substrate dissolved in dry dimenthylformamide, sodium hydride was added and the mixture was stirred at room temperature for about two hours. A suitable haloalkyl carboxyester was added to the above reaction mixtures and the mixture was stirred at room temperature for 16–20 hours. The reaction was worked up as described in Method I of Example 2 to yield pure 17 and/or 20-carboxyalky carboxylate derivative. Examples of haloalkyl carboxy esters that can be used are chloro or bromo derivative of methyl or ethyl acetate, or chloro or bromo derivative of propionate and the like.

EXAMPLE 7

Preparation of 17 and/or 20-carboxyalkyl Carboxylic Acid 17 and/or 20-carboxyalkyl carboxylate was dissolved in an alcoholic solvent such as methanol, ethanol, propanol or the like to which a hydroxide such as sodium or potassium hydroxide or the like was added. The mixture was warmed to 40–50° C. for 2–4 hours. The reaction was worked up as described in Method I of Example 2 to yield pure 17 or 20 -carboxyalkyl carboxylic acid derivative.

EXAMPLE 8

Preparation of 2-bromo-3-oxo-derivative 3-oxo-dihydrobetulinic acid derivative was dissolved in halogenated organic solvent such as CCl$_4$,CH$_2$,Cl$_2$, CHCl$_3$ or the like. Liquid bromine dissolved in the same solvent was added dropwise while maintaining the temperature between 0–10° C. The reaction mixture was brought to room temperature and maintained for a few hours. The mixture was worked up in the usual manner, the organic layer was washed with 5–10% aqueous alkaline solution followed by water. Evaporation and crystallization yielded pure 2-Bromo-3-oxo derivatives. Examples of aqueous alkaline solution that can be used are bicarbonate or carbonate of an alkali metal in water, and the like.

EXAMPLE 9

Preparation of 20, 29-dibromo Derivative

Betulinic acid or its derivative (except 3-oxo-betulinic acid or its derivatives) was dissolved in halogenated organic solvent. To this liquid bromine dissolved in the same solvent was added dropwise and temperature maintained between 0–10° C. The reaction mixture was brought to room temperature and stirred for few hours. The reaction mixture was worked up as described in Method I of Example 2. The organic layer was washed in 5–10% aqueous alkaline solution and evaporated. The crystallized product yield pure 20,29-dibromo derivative.

Examples of halogenated solvents that can be used are CCl$_4$,CH$_2$Cl$_2$,CHCl$_3$ and the like.

EXAMPLE 10

Preparation of 3-amino Derivatives a] 3-oximino derivative is dissolved in glacial acetic acid and shaken under hydrogen atmosphere (60–70psi) in presence of platinum oxide catalyst for several hours. Reaction mixture is filtered, mother liquor evaporated under vacuum to remove glacial acetic acid and the residue worked up in the usual manner to yield the corresponding 3-amino derivative.

b] 3 oxo-derivative is dissolved in methanol added ammonium sulphate and sodium borohyride and refluxed for 2–4 hrs. Reaction mixture evaporated to dryness added water, filtered the solid and crystallized to give 3-amino derivatives.

EXAMPLE 11

Preparation of 3-o-benzoyl Derivatives

Substrate in organic base is treated with suitable benzoyl chloride for approximately 6–16 hours at an ambient temperature. Examples of benzoyl chloride that can be used are represented by general formula $C_6HnXCOCl$ (n=2 to 4) $C_1OH$, X COCl [X=H, Cl, Br, I, F, $CF_3$ $CHCl_2$, $C_6H_5$, OH, $OCH_3$, $OC_2H$, $OC_3H_7$, $C_nH_{2n}+1$(n=1 to 7)]. The reaction was worked up by addition of water and extraction with organic solvent. The organic layer was dried over anhydrous sodium sulphate, evaporated and residue crystallized to yield pure 3-o-benzoyl derivatives respectively. Examples of organic bases that can be used are pyridine, piperidine.

EXAMPLE 12

Preparation of 3-o-mesylate Derivatives

Substrate is dissolved in halogenated solvent and added methane sulphonyl chloride slowly to it at 5–10° C. Stirred the mixture at an ambient temperature for 2–4 hours. Worked up the reaction mixture by washing the organic layer with water. Organic layer dried over anhydrous sulfate, filtered, evaporated to dryness to get a residue which was crystallized from acetonitrile to yield pure 3-o-mesylate derivative.

EXAMPLE 13

Preparation of 3-phenyl Hydrazino or its Phenyl Substituted Derivative 3-phenylhydrazone or its phenyl substituted derivative of betulinic acid or dihydrobetulinic acid is dissolved in glacial acetic acid and shaken under hydrogen atmosphere (50–70 psi) in presence of platinum sponge catalyst for 3–5 hours. Reaction mixture was filtered, mother liquor evaporated under vacuum to remove glacial acetic acid and the residue crystallized from alcoholic solvent to yield pure 3-phenyl hydrazino or its phenyl substituted derivative. Alcoholic solvents used are methanol, ethanol or iso propanol.

EXAMPLE 14

Preparation of 3-N-hydroxyethyl Derivative 3-oxo-derivative is dissolved in absolute alcoholic solvent such as methanol/ethanol and to it added 15–20% alcoholic hydrochloric acid and 2-aminoethanol and stirred at room temperature for 30–60 minutes. To this added sodium cyanoborohydride and further stirred at room temperature for approximately 72 hours. Worked up by adding water followed by filtration of solid to yield crude product, which was crystallized from alcohol to yield pure 3-N-hydroxyethyl derivative.

EXAMPLE 15

Preparation of 3-N-benzylidene Derivative 3-amino derivative is dissolved in alcoholic solvent, such as methanol/ethanol and to it added benzaldehyde or substituted benzaldehyde derivative in presence or absence of alkali carbonate, such as sodium or potassium carbonate. The mixture was stirred for few hours at ambient temperature to 50° C. approximately. The reaction mixture was worked up by removing alcohol under vacuum and addition of water. The aqueous layer either filtered or extracted with halogenated organic solvent, followed by evaporation yielded 3-N-benzylidene derivative.

EXAMPLE 16

Preparation of 3-O-benzene Sulphonate Derivatives (a) dissolving the substrate in halogenated organic solvent, adding few drops of pyridine followed by benzene sulphonyl chloride or its benzene substituted derivative slowly keeping the temperature between 5 to 10° C.

(b) stirring the mixture at an ambient temperature for few hours.

(c) working up the reaction mixture by washing the organic layer with water.

d) drying the organic layer over anhydrous sodium sulfate, filtering, evaporated to get a residue which is crystallized from nitrite or alcoholic solvent to yield pure 3-O-bezene sulphonate derivative

EXAMPLE 17

Preparation of 3-O-sulplhonamide Derivatives a) dissolving 3-amino derivative in halogenated organic solvent adding few drops of triethylamine followed by alkyl or benzene sulphonyl chloride or its substituted derivative slowly keeping the temperature between 5–10° C.

b) stirring the mixture at an ambient temperature for few hours.

c) working up the reaction mixture by washing with water.

d) drying the organic layer over anhydrous sodium sulphate, filtering, evaporating to dryness to get a residue which is crystallized to yield pure 3-O-sulphonamide derivatives.

EXAMPLE 18

30 μl of ECV304 cell suspension (50×10$^4$ cells/ml in RPMI 1640 containing 10% FBS) followed by 150 μl of medium was added to the wells of a 96-well tissue culture plate (Nunc, Denmark) and incubated (37° C., 5% $CO_2$) overnight. 20 μl of the betulinic acid derivative to be tested was then added at concentrations ranging from 0.5 μg/ml to 4 μg/ml. Each concentration was plated in triplicates. 20μl of medium alone was added to control wells. After 72 hours of incubation an MTT assay (Mosmann, 1983) was performed and percentage inhibition in proliferation of treated cells was calculated with respect to control cells.

The cytotoxicity assays for tumor cells have been described in detail in our application Ser. No. 09/040,856 filed in U.S. on Mar. 18, 1998. Table I shows the $ED_{50}$ values against ECV304 and four different tumor cell lines and the endothelial cell specificities of seventeen potent derivatives.

TABLE 1

| | Endothelial | Prostate | | Lung | | Ovary | | Colon | |
|---|---|---|---|---|---|---|---|---|---|
| S. No Derivative | ECV304 ($ED_{50}$) | DU145 ($ED_{50}$) | ECS Ratio | L132 ($ED_{50}$) | ECS Ratio | PA-1 ($ED_{50}$) | ECS Ratio | HT-29 ($ED_{50}$) | ECS Ratio |
| 1 MJ353-RS | 2.4 | 6.5 | 2.7 | 4.5 | 1.9 | 5 | 2.08 | >10 | 4.2 |
| 2 MJ548-RS | 2.5 | >10 | >4 | >10 | >4 | 3.9 | 1.56 | >10 | 4.0 |
| 3 MJ878-RS | 0.5 | 9.9 | 19.8 | 0.8 | 1.6 | 3.5 | 7.0 | 1.75 | 3.5 |
| 4 MJ912-RS | 0.4 | 8.5 | 21.1 | >4 | >10 | ND | — | 0.35 | 0.87 |
| 5 MJ935-RS | 0.7 | 3.2 | 4.5 | 1.2 | 1.7 | ND | — | >10 | >14.3 |
| 6 MJ937-RS | 0.7 | 2.5 | 3.5 | 1.1 | 1.5 | 1.6 | 2.3 | 1.7 | 2.4 |
| 7 MJ939-RS | 0.9 | >10 | >11.1 | 2.7 | 3.0 | >4 | >4.4 | >10 | >11.1 |
| 8 MJ943-RS | 2.6 | >4 | >1.5 | 4 | 1.5 | >4 | >1.53 | >10 | 3.84 |
| 9 MJ998-RS | 0.35 | 2.2 | 6.2 | 2.5 | 7.1 | 1.3 | 3.7 | 4 | 11.4 |
| 10 MJ1065-RS | 2.4 | 2.5 | 1.04 | 3.4 | 1.4 | 1.3 | 0.54 | 4.9 | 2.04 |
| 11 MJ1098-RS | 0.6 | 1.5 | 2.5 | 1.3 | 2.1 | 1.6 | 2.7 | 2.6 | 4.3 |
| 12 MJ1101-RS | 4.0 | >10 | >2.5 | 1.7 | 0.43 | >4 | >1 | >10 | 2.5 |
| 13 MJ1103-RS | 2.0 | >4 | >2.0 | 4 | 2.0 | 1.5 | 0.75 | 10 | 5.0 |
| 14 MJ1104-RS | 1.9 | 2 | 1.05 | 5.9 | 3.1 | >4 | >2.1 | 3.5 | 1.84 |
| 15 MJ1108-RS | 1.8 | 1 | 0.55 | 4.6 | 2.5 | ND | — | >10 | >5.6 |
| 16 MJ1138-RS | 1.7 | >10 | >5.8 | 7 | 4.1 | >4 | >2.3 | >10 | >5.89 |
| 17 MJ1161-RS | 4.0 | 0.4 | 0.1 | 3.5 | 0.88 | 2.6 | 0.65 | 3.5 | 0.87 |

$ED_{50}$ = Concentration ($\mu$g/ml) of drug that causes 50% Cytotoxicity, where
Percent Cytotoxicity = $[1 - O.D._{Treated}/O.D._{Control}] * 100$
ECS ratio = $ED_{50}$ Tumor cell growth/$ED_{50}$ Endothelial cell growth.
ECS less than 10 = Low ECS
ECS between 10 and 20 = Moderate ECS
ECS greater than 20 = High ECS We predict that the 'high' and 'moderate' ECS compounds specifically target endothelial cells and can be grouped under potent anti-angiogenic compounds while low ECS compounds would supplement their already reported cytotoxic activity against tumor cells.

EXAMPLE 19

Several derivatives of betulinic acid were prepared by making substitutions and/or structural changes at $C_3$, $C_{17}$, $C_{20}$, and/or $C_{29}$ positions of betulinic acid as described in the examples. The derivatives were characterized on the basis of spectral data. Table II refers to the structures of FIG. 2 wherein R to $R_4$ which are clearly indicated including lists the structures of forty derivatives. FIG. 2 wherein R to $R_4$ are shown herebelow:

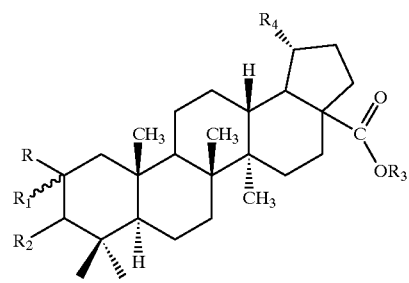

FIG.-2

TABLE II

| DERIVATIVE | R | R1 | R2 | R3 | R4 |
|---|---|---|---|---|---|
| MJ353-RS | H | H | =$NNHC_6H_5$ | H | $CH_2$=$CCH_3$ |
| MJ548-RS | H | Br | =O | $CH_2CH_2COOCH_3$ | $BrCH_2$—$C(Br)CH_3$ |
| MJ878-RS | H | H | —$NHNHC_6H_5$ | H | —$CH(CH_3)_2$ |
| MJ912-RS | H | H | —$NHNHC_6H_4(OCH_3)$[4] | H | —$CH(CH_3)_2$ |
| MJ935-RS | H | H | —$OCO$—$C_6H_3F_2$[3,5] | H | —$CH(CH_3)_2$ |
| MJ937-RS | H | H | —$OCO$—$C_6H_3F_2$[2,4] | H | —$CH(CH_3)_2$ |
| MJ939-RS | H | H | —$OCOC_6H_4(CF_3)$[3] | H | $CH_2$=$C$—$CH_3$ |
| MJ943-RS | H | H | —$OCOC_6H_4(CF_3)$[2] | H | —$CH(CH_3)_2$ |
| MJ998-RS | H | H | —$N$=$CHC_6H_3F_2$[3,4] | H | —$CH(CH_3)_2$ |
| MJ1065-RS | H | H | —$N$=$CHC_6H_3F_2$(2,4) | H | —$CH(CH_3)_2$ |
| MJ1098-RS | H | H | —$NOCH_2C_6H_4NO_2$(4) | H | —$CH(CH_3)_2$ |
| MJ1101-RS | H | H | —OH | $COCH_2$=$CH_2$ | $CH_2$=$C$—$CH_3$ |
| MJ1103-RS | H | H | —OH | $COCH_2$=$CH_2$ | —$CH(CH_3)_2$ |
| MJ1104-RS | H | H | —$OCOC_6H_4(C_5H_{11})$[4] | H | $CH_2$=$C$—$CH_3$ |
| MJ1108-RS | H | H | —$OCOCH_2C_6H_3(OCH_3)_2$[2,5] | H | $CH_2$=$C$—$CH_3$ |
| MJ1138-RS | H | H | —$OCOC_6H_4(C_7H_{15})$[4] | H | $CH_2$=$C$—$CH_3$ |
| MJ1161-RS | H | Br | =O | 3-deoxy DHBA* | —$CH(CH_3)_2$ |
| MJ1183-RS | H | H | —$OCOCH_2C_6H_3(OCH_3)_2$[3,4] | H | $CH_2$=$C$—$CH_3$ |
| MJ1204-RS | H | H | =O | $COCH$=$CH_2$ | —$CH(CH_3)_2$ |
| MJ1205-RS | H | H | —$OCOC_6F_5$ | H | $CH_2$=$C$—$CH_3$ |
| MJ1210-RS | H | H | =NOH | $COCH$=$CH_2$ | —$CH(CH_3)_2$ |

TABLE II-continued

| DERIVATIVE | R | R1 | R2 | R3 | R4 |
|---|---|---|---|---|---|
| MJ1213-RS | H | H | —$OCOC_6F_5$ | H | —$CH(CH_3)_2$ |
| MJ1283-RS | H | H | —$OCOC_6H_3(OCH_3)_2[3,4]$ | H | —$CH(CH_3)_2$ |
| MJ1287-RS | H | H | —$OCOC_6H_3(OCH_3)_2[2,4]$ | H | —$CH(CH_3)_2$ |
| MJ1295-RS | H | H | —$OCOCClF_2$ | H | —$CH(CH_3)_2$ |
| MJ1296-RS | H | H | —$OCOC_6H_4$—$C_6H_5(4)$ | H | $CH_2$=C—$CH_3$ |
| MJ1298-RS | H | H | —OCOCH(Cl)Ph | H | $CH_2$=C—$CH_3$ |
| MJ1301-RS | H | H | —OCO—$(CH_2)_3$COOH | H | —$CH(CH_3)_2$ |
| MJ1304-RS | H | H | —$OCOC_6H_4Cl(4)$ | H | $CH_2$=C—$CH_3$ |
| MJ1305-RS | H | H | —$OCOC_6H_4Cl(4)$ | H | —$CH(CH_3)_2$ |
| MJ1315-RS | H | H | —$OCOC_6H_4(CHCl_2)(3)$ | H | $CH_2$=C—$CH_3$ |
| MJ1316-RS | H | H | —$OCOC_6H_4(CHCl_2)(3)$ | H | —$CH(CH_3)_2$ |
| MJ1312-RS | H | H | —$OSO_2CH_2CH_2CH_2Cl$ | H | $CH_2$=C—$CH_3$ |
| MJ1313-RS | H | H | —$OSO_2CH_2CH_2CH_2Cl$ | H | —$CH(CH_3)_2$ |
| MJ1327-RS | H | H | —$OCOC_6H_2(COOH)(2)Cl_2(3,6)$ | H | $CH_2$=C—$CH_3$ |
| MJ1328-RS | H | H | —$OCOC_6H_2(COOH)(2)Cl_2(3,6)$ | H | —$CH(CH_3)_2$ |
| MJ1335-RS | H | H | —OCOCH(Cl)—$CH_3$ | H | $CH_2$=C—$CH_3$ |
| MJ1336-RS | H | H | —OCOCH(Cl)—$CH_3$ | H | —$CH(CH_3)_2$ |
| MJ1338-RS | H | H | =$NNHCOC_6H_4(OH)(2)$ | H | —$CH(CH_3)_2$ |
| MJ1366-RS | H | Br | =N—O—$CH_2C_6H_4NO_2(4)$ | H | —$CH(CH_3)_2$ |

*Dihydrobetulinic acid

EXAMPLE 20

Matrigel (70 μl) was placed into each well of a 96-well culture plate at 4° C. and was allowed to polymerize by incubation at 37° C. for 30 min. ECV304 ($1\times10^4$) cells were seeded on the Matrigel in 200 μl DMEM containing 10% FBS. Betulinic acid and derivatives to be tested were added to marked wells at non-cytotoxic concentrations and incubated at 37° C. for 24–48 hours. The absence of cytotoxicity of betulinic acid and its derivatives on ECV304 cells at the above time points was confirmed by suitable controls. Five different phase-contrast microscopic fields (4x) were viewed and total tube area of the tube-like-structures (TLS) measured using Video Pro 32 Image Analysis system. Percent reduction in total tube area was given as the mean of the data from five fields. Percent inhibition of TLS was calculated with reference to Controls(no drug).

TABLE III

| | % reduction in total tube area at concentration | | |
|---|---|---|---|
| Derivative | 0.5 μg/ml | 2 μg/ml | 4 μg/ml |
| MJ937-RS | 16.7 | 21 | 21.7 |
| MJ998-RS | 21.1 | 13.4 | 33.4 |
| MJ1065-RS | 23.4 | 16.7 | 46.7 |
| MJ1098-RS | 15 | 7.5 | 10 |
| MJ1161-RS | 18.4 | 16.7 | 11.7 |

EXAMPLE 21

A suitable formulation of betulinic acid derivatives was prepared as follows. The derivatives were solubilized in a minimum volume of methanol. The derivatives may also be solubilized in isopropyl alcohol, dimethylformamide, dimethylslulfoxide or any other suitable solvent. Substituted beta-cyclodextrin, such as 2-hydroxypropyl beta-cyclodextrin, sulfobutyl ether beta-cyclodextrin was separately dissolved in water to a concentration of approximately 50 to 1000 mg per ml, preferably 250 to 750 mg per ml. The solubilized betulinic acid derivative was added in small aliquots to the derivatized beta cyclodextrin solution and sonicated at low temperature until a clear solution developed. The organic solvent was then removed by rotary evaporation and the final solution filtered to give a sterile product. The resulting solution was lyophilized.

Systemic administration refers to oral, rectal, nasal, transdermal and parentral (i.e., intramuscular, intraperitoneal, subcutaneous or intravenous). In accordance with good clinical practice, it is preferred to administer the composition at a dose that will produce antiangiogenic effects without causing undue harmful side effects. The composition may be administered either alone or as a mixture with other therapeutic agents.

Pharmaceutical compositions which provide from about 10 mg to 1000 mg of the composition per unit dose are preferred as tablets, lozenges, capsules, powders, aqueous or oily suspensions, syrups, elixirs, implants or aqueous solutions by any conventional method. The nature of pharmaceutical composition employed will, of course, depend on the desired route of administration. The human dosage of the composition is in the range of 1.0 to 200 mg/kg/day and the preferred range is 1.0 to 50 mg/kg/day.

One embodiment of the invention relates to a method of using novel betulinic acid derivatives or a combination thereof to treat a patient with tumor associated angiogenesis by administering a pharmaceutically effective dosage of said betulinic acid derivative or its combination to the patient. The patient of the invention can be human, mammal or other animal. The $ED_{50}$ value of betulinic acid derivatives against human umbilical vein endothelial cells is 0.35 to 4.0 μg/ml. The endothelial cell specificity of betulinic acid derivatives for prostate cancer is 1.04 to 21.1. As regards the endothelial cell specificity of betulinic acid derivatives for lung cancel is 0.43 to >10. However, regarding the endothelial cell specificity of betulinic acid derivatives for ovarian cancel is 0.54 to 7.0. With regard to the endothelial cell specificity of betulinic acid derivatives for colon cancer is 0.87 to 14.3.

The betulinic acid derivative is administered to the patient in a pharmaceutically acceptable additive, carrier, diluent, solvent, filler, lubricant, excipient, binder or stabilizer. Preferably, the betulinic acid derivative is administered in the form of a tablet, lozenge, capsule, powder, aqueous or oily suspension, syrup, elixir, implant or aqueous solution and the betulinic acid derivative or derivatives or combination thereof is administered to the patient systemically.

What is claimed is:

1. A betulinic acid derivative of structure (3)

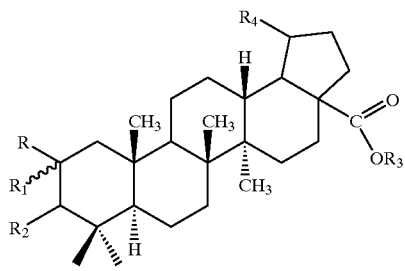

where

R is H;

$R_1$ is H or Br;

$R_2$ is O, $NNHC_6H_5$, $NHNHC_6H_5$, $NHNHC_6H_4(OH_3)(4)$, $N=CHC_6H_3F_2$ (3,4), $N=CHC_6H_3F_3$ (2,4), NOH, $NNHCOC_6H_4OH(2)$ or $NOCH_2C_6H_4NO2$ (4);

$R_3$ is H, $-CH_2CH_2COOCH_3$, $-COCH=CH_2$, or 3-Deoxydihydrobetulinic acid; and $R_4$ is $CH_2=C-CH_3$ $CH(CH_3)_2$ or $BrCH_2C(Br)CH_3$ with the proviso that the following compounds are excluded;

$R_2$ is not O or NOH, when R, $R_1$ and $R_3$ are H, and $R_4$ is $CH_2=CCH_3$ or $CH(CH_3)_2$.

* * * * *